(12) United States Patent
Thuillier

(10) Patent No.: US 10,584,994 B2
(45) Date of Patent: Mar. 10, 2020

(54) SENSING DEVICE FOR SENSING A GAS AND METHOD FOR ESTIMATING A VOLUME OF A SENSED GAS

(71) Applicant: BoydSense, Inc., San Bruno, CA (US)

(72) Inventor: Bruno Thuillier, San Francisco, CA (US)

(73) Assignee: BoydSense, Inc., San Bruno, CA (US)

( * ) Notice: Subject to any disclaimer, the term of this patent is extended or adjusted under 35 U.S.C. 154(b) by 128 days.

(21) Appl. No.: 15/389,726

(22) Filed: Dec. 23, 2016

(65) Prior Publication Data

US 2017/0191860 A1 Jul. 6, 2017

(30) Foreign Application Priority Data

Dec. 30, 2015 (EP) .................................... 15307179

(51) Int. Cl.
| | |
|---|---|
| *G01N 33/497* | (2006.01) |
| *G01F 22/02* | (2006.01) |
| *G01N 29/02* | (2006.01) |
| *G01L 9/00* | (2006.01) |
| *G01N 27/12* | (2006.01) |

(Continued)

(52) U.S. Cl.
CPC ............ *G01F 22/02* (2013.01); *G01L 9/0072* (2013.01); *G01N 27/125* (2013.01); *G01N 29/02* (2013.01); *G01N 33/0027* (2013.01); *G01N 33/497* (2013.01); *G01N 33/4972* (2013.01);

(Continued)

(58) Field of Classification Search
CPC .......................... G01N 33/4972; G01N 33/497
See application file for complete search history.

(56) References Cited

U.S. PATENT DOCUMENTS

| | | | |
|---|---|---|---|
| 2007/0048181 A1* | 3/2007 | Chang .................... | B82Y 15/00 422/400 |
| 2014/0061043 A1* | 3/2014 | Stock .................... | G01N 33/497 204/403.01 |

(Continued)

FOREIGN PATENT DOCUMENTS

CN          102809400          12/2012

OTHER PUBLICATIONS

Rabbani K S et al: "A Novel Gas Flow Sensor Based on Sound Generated by Turbulence", Instrumentation and Measurement Technology Conference, 1997, IMTC/97. Proceedings, Sensing, Processing, Networking., IEEE Ottawa, Ont., Canada May 19-21, 1997, New York, NY, USA, IEEE, US, vol. 2, May 19, 1997 (May 19, 1997), pp. 1386-1388, XP010233794, DOI: 10.1109/IMTC. 1997.612426 ISBN: 978-0-7803-3747-3.

(Continued)

*Primary Examiner* — Paul S Hyun
(74) *Attorney, Agent, or Firm* — Barnes & Thornburg LLP; Jeffrey R. Stone

(57) ABSTRACT

The invention relates to a sensing device for a portable apparatus, in particular a portable telecommunication device or a wearable device, the sensing device comprising an acoustic wave sensing mechanism, like a microphone; and a gas sensing mechanism, wherein the acoustic wave sensing mechanism and the gas sensing mechanism are integrally formed. The invention furthermore relates to an electronic device comprising such a sensing device. In addition, a method is provided that allows calibrating a gas volume based on an output signal of an acoustic wave sensing mechanism.

12 Claims, 3 Drawing Sheets

Figure 1:
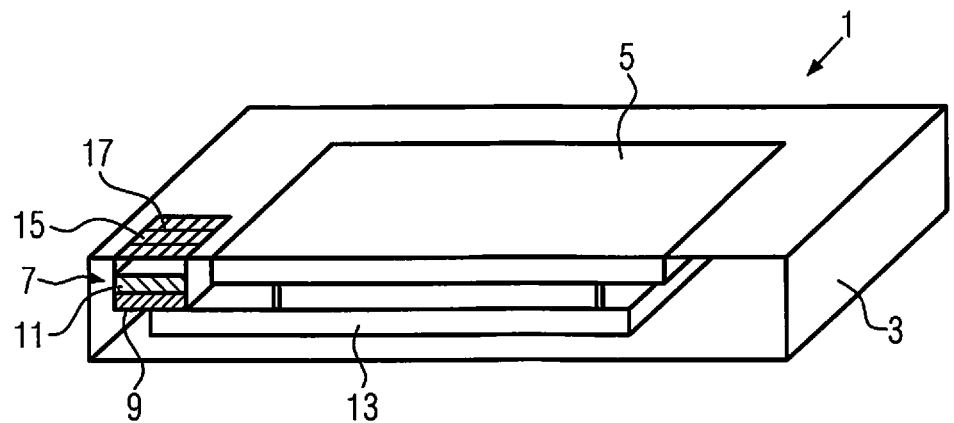

(51) Int. Cl.
*G01N 33/00* (2006.01)
*H04R 19/04* (2006.01)
(52) U.S. Cl.
CPC ......... *H04R 19/04* (2013.01); *H04M 2250/12* (2013.01); *H04R 2201/003* (2013.01)

(56) References Cited

U.S. PATENT DOCUMENTS

| | | | |
|---|---|---|---|
| 2014/0165698 A1* | 6/2014 | Mochizuki | G01N 33/4972 73/23.3 |
| 2014/0208829 A1 | 7/2014 | Lechner et al. | |
| 2015/0226586 A1 | 8/2015 | Yang | |

OTHER PUBLICATIONS

European Search Report issued in EP 15307179 and dated Aug. 17, 2016.

* cited by examiner

SENSING DEVICE FOR SENSING A GAS AND METHOD FOR ESTIMATING A VOLUME OF A SENSED GAS

The invention relates to a sensing device for sensing gas. It furthermore relates to a portable device comprising such sensing device and to a method for estimating the volume of the sensed gas.

Such sensing devices are known to consumers in the form of fire detectors for their houses thus measuring parameters of the ambient air or in the form of breath testers, e.g. to estimate the amount of alcohol consumed.

Those sensors known are typically rather voluminous and have a high energy consumption. This makes it rather difficult to integrate them into portable electronic devices, like smart phones or in general wearables, to provide the user with gas sensing capabilities, e.g. for monitoring their environment or their health within the electronic device they use to communicate or work with on a regular basis.

In addition, those gas sensors are rather costly, which is in particular related to the gas volume determining functionality they have to satisfy. Indeed, to be able to obtain the concentration of a given molecule in the ambient air or the breath of the user, a calibration of the air volume to be analysed has to be carried out. In the case of breath testers, a precise calibration is necessary and achieved by using a rather voluminous and expensive mechanism with admission and exhaust pipes and a mechanical spring loaded switch, which allows the air flow to enter the analyzing chamber as long as the calibrated volume has not yet been achieved and then switches the piping system such that additional air is exhausted directly via the exhaust pipe without entering the measurement chamber.

Other approaches try to get rid of the mechanical parts of the volume calibration by trying to model the gas flow using software algorithms based on statistical data, the geometry of the device and/or the gas admission time. Up to now, these models did not provide sufficiently reliable results.

It is therefore an object of the present invention to provide a gas sensing means that overcomes the problems observed in the art. In particular, it is the object of the present invention to provide a gas sensing device that simplifies its integration into electronic devices and/or that allows a simplified yet reliable calibration.

The first object of the invention is achieved by a sensing device comprising: an acoustic wave sensing means, in particular a microphone and a gas sensing means, wherein the acoustic wave sensing means and the gas sensing means are provided in one device, in particular integrally formed. The sensing device can be used in a portable device, in particular a communication device or a wearable. This kind of sensing device is compact and needs much less space than a separate microphone and gas sensor. In particular, it only needs one hole in the housing of a portable device.

According to a variant, the acoustic wave sensing means and the gas sensing means can be incorporated into the same housing. Thus only one packaging for both functionalities is necessary and the volume occupied by the one housing is smaller than for the sum of the housing of the acoustic wave sensing means and the gas sensing means.

According to a variant, the sensing device can be arranged in an array or in a stack of sensors. Thus the same flexibility with a standard gas sensor can also be achieved with the combined functionality sensing device.

According to a variant, the acoustic wave sensing means can be provided over a substrate and the gas sensing means can be stacked over the acoustic wave sensing means. By stacking them one over the other, the footprint necessary to realize the sensing device remains the same as for a microphone alone. In addition, by stacking them one over the other, in particular aligned along the thickness direction of the sensing device, the two integrated sensors experience essentially the same conditions, e.g. concerning temperature, gas flow and the like.

According to a variant, the microphone can be a microelectromechanical system (MEMS) microphone. Such devices can be highly integrated.

According to a variant, the gas sensing means can be based on at least one of a metal oxide (MOX), in particular a tin oxide, carbon nanotubes (CNTs), a gold nanoparticle, a silicon nanowire, a quartz crystal microbalance (QCM), a colorimetric sensor, and a conductive polymer. These technologies provide reliable results and at the same time have a low energy consumption, in particular the nanotubes. Furthermore their fabrication can be integrated with the fabrication process of the acoustic wave sensing means and a common CMOS base can be used. Mox based gas sensing has the advantage of being non selective whereas other technologies like the carbon nanotubes are selective.

According to a variant, the gas sensing means can be arranged in or on or over a movable plate or in or on or over a fixed plate of the acoustic wave sensing means. By providing the gas sensing means directly on one of the layers of the acoustic wave sensing means the design of the device can be simplified. In particular, according to a variant, a hot plate as part of the gas sensing means could be part of the movable plate or the fixed plate of the acoustic sensing means. This would further reduce the fabrication costs.

According to a variant, the gas sensing means can comprise a plurality of perforations preferably aligned with perforations of the fixed plate of the acoustic wave sensing means in the thickness direction of the sensing device. By aligning the perforations both sensing functionalities essentially experience the same gas flow parameters.

According to a variant, the device can further comprise a membrane, wherein the sensing device is configured such that a reference volume of a gas sensed by the gas sensing means is determined based on a signal representative of a movement and/or deformation of the membrane. As the movement and/or the deformation of the membrane is related to the pressure exerted by the entering gas flow and the duration of the gas flow, it provides information about the gas volume entering the sensing device and can therefore be used to calibrate the gas volume to be analysed. The signals are typically analog or digital electric signals.

According to a variant, the membrane can be the movable plate of the acoustic wave sensing means. Thus elements of the acoustic wave sensing means can be used to calibrate the gas volume to be sensed by the gas sensing means.

According to a variant, the sensing device can further comprise an analog-to-digital converter and/or processing means, in particular provided on said substrate, wherein the integrated microphone and gas sensing means share at least partially said analog-to-digital converter and/or processing means. By sharing resources the device can be further reduced in size. Thus further resources can be shared by the two sensing means even further reducing the size of the device.

According to a variant, the acoustic wave sensing means and the gas sensing means are arranged side-by-side on the same substrate.

The object of the invention is also achieved with a portable electronic device, in particular communication device, comprising a sensing device as described above.

With such an inventive device it becomes possible to provide gas sensing functionalities without having to add an additional sensor, as the gas sensing functionality is incorporated into the acoustic sensing means, e.g. the microphone.

According to a variant, the portable electronic device can further comprise a housing with a hole, wherein both the gas sensing means and the acoustic wave sensing means of the sensing device are positioned within and/or aligned with the same hole. Thus, without having to add an additional hole into the housing of the portable electronic device, it becomes possible to add a new functionality to the device, namely gas sensing to monitor the environment or to monitor some health indicators.

The second object of the invention is achieved by a method for determining a volume of a gas in a gas flow comprising a step of determining the volume based on a signal representative of a movement and/or deformation of a membrane. To be able to determine a concentration of a certain molecule and or of certain molecules in a gaseous flow it is not necessary to identify the nature of the molecules but also to determine the volume of the gas to be analysed or to collect gas until a predetermined volume is obtained. The invention takes advantage of the fact that due to the pressure of the gas flow, e.g. the breath of a user, a membrane can move and/or deform. Thus by knowing the movement and/or the deformation, an indicator for the gas volume present is obtained. Knowing further parameters of the device, like the size of the membrane, etc. it becomes possible to determine the gas volume to be analysed inside the device.

According to a variant, the membrane is a movable plate of an acoustic wave sensing means, in particular a microphone. Such acoustic wave sensing means are readily available in personal electronic devices, in particular communication devices and/or wearables, and comprise a moveable plate that flexes and/or deforms under the pressure of the human speech. Thus, it will also flex under the impact of the breath of a user, or by any other gas flow, like ambient air, entering the acoustic sensing means. It is thus not necessary to add a new element into such a personal electronic device, so that the integration of a gas sensor in such a device is simplified.

According to a variant, the volume determination comprises using pressure data relative to the pressure exerted by the gas flow on the membrane is obtained from the signal and/or timing data relative to a duration during which pressure is exerted on the membrane. The use of these parameters which can be obtained from the signals received from the membrane enable the determination of the volume.

According to a variant, the method can use a sensing device as described above or a portable device as described above and the volume of gas is determined based on a signal of the acoustic wave sensing means.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages. The various features of the embodiments described can be combined to obtain further variants according to the invention.

Figure 2:
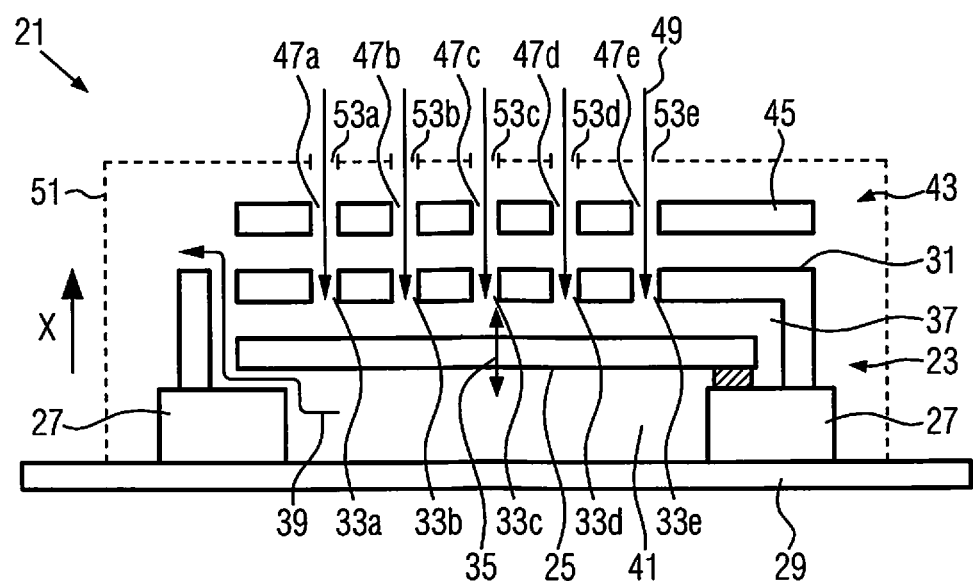
Figure 3:
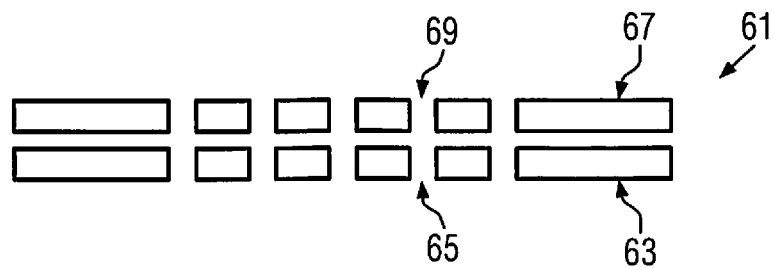
Figure 4:
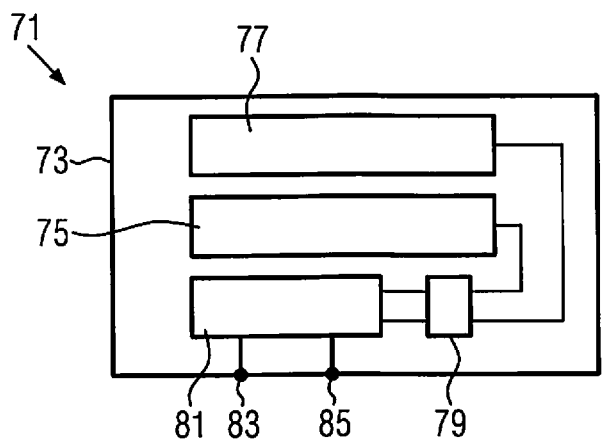
Figure 5:
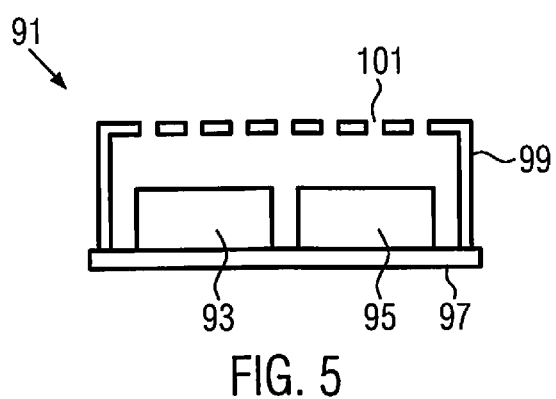
Figure 6:
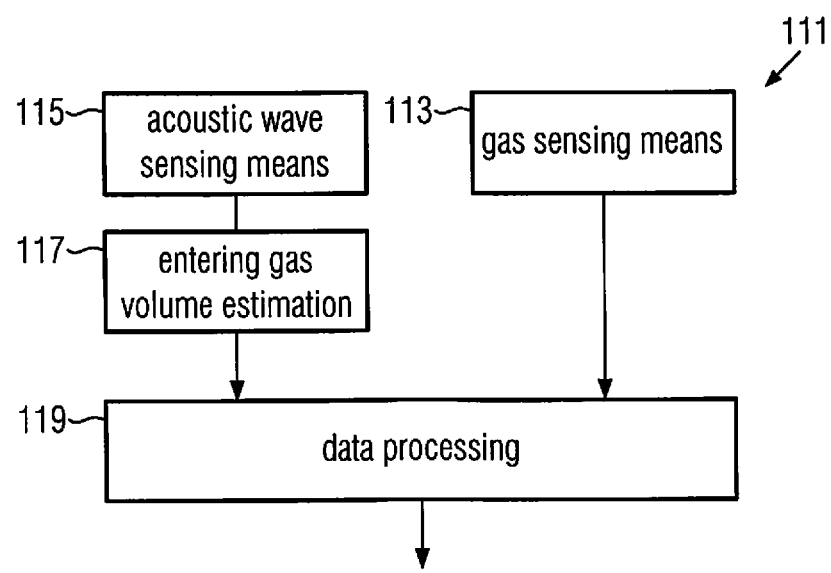

The above and other objects and features of the present invention will become more apparent from the following description and preferred embodiments given in conjunction with the accompanying drawings in which:

FIG. 1 illustrates an electronic device with a sensing device according to the invention, FIG. 2 illustrates schematically an embodiment of the sensing device according to the invention, FIG. 3 illustrates schematically a metal oxide gas sensing device according to the invention, FIG. 4 illustrates a block diagram of a further embodiment of the sensing device according to the invention, FIG. 5 illustrates a further embodiment of the sensing device according to the invention wherein the acoustic wave sensing means and the gas sensing means are arranged side by side, and FIG. 6 illustrates a block diagram of a method to estimate the volume of a gas according to the invention.

FIG. 1 illustrates schematically a cut through an electronic device 1 according to a first embodiment of the invention, here in particular a mobile communication device, comprising a housing 3, a display device 5 and a sensing device 7 with an acoustic wave sensing means, here a microphone 9, and a gas sensing means 11, connected to a motherboard 13 comprising the various chips and electrical interconnections as well as input/output means (not shown) for data processing of the electronic device 1. The sensing device 7 is placed into an opening 15 or a hole present in the housing 3. Here, the opening 15 is covered by a grid 17, protecting the sensing device 7 against dirt, like dust particles. In addition, means to protect against humidity can be added according to a variant. The sensing device could also be positioned such that it is underneath the hole 15 in the housing 3 but aligned with it.

The electronic device 1 can be a mobile phone, a smart phone, a tablet, a laptop, a personal electronic assistant, a tracking device, an electronic wearable or the like.

According to the invention, the sensing device 7 combines the functionality of a microphone 7 enabling acoustic inputs to the electronic device 1, and stacked thereon the gas sensing means 11 for analyzing gases that enter the sensing device 7 into one sensor. The gas sensing means 11 can be configured to analyse the ambient air, e.g. to check the air quality, and/or to analyse a users breath, e.g. to carry out a breath test or to identify certain molecules indicative of a disease.

By stacking the gas sensing means 11 onto the microphone and thereby combining two functionalities that base their output signals on physical and/or chemical properties of a gas entering the sensing device 7, it becomes possible to use just one and the same hole 15 in the housing 3. This keeps the design of the housing 3 and the electronic device 1 simple and cost effective. Indeed, each hole in the housing 3 makes the design more complex as protection against dust and moisture has to be provided and further also leads to unwanted design constraints.

FIG. 2 illustrates an enlarged view of a sensing device 21 according to a second embodiment of the invention. The sensing device 21 could for instance be used as sensing device 7 in the electronic device shown in FIG. 1.

The sensing device 21 comprises an acoustic wave sensing means, here a microphone 23. The microphone 23 in this embodiment is a MEMS microphone readily used in mobile phones like smart phones. A MEMS microphone is an acoustic transducer transforming acoustic signals into electrical signals. The microphone 23 comprises a movable plate 25 arranged on a pillar structure 27a, 27b over a substrate 29. The pillar structure can also be obtained by providing a cavity inside the substrate 29. The microphone 23 furthermore comprises a stiff plate 31, also called back plate or fixed plate, arranged over and at a distance of the movable plate 27. The stiff plate 31 comprises holes 33a-33e.

The movable plate 27 and the stiff plate 31 form a capacitor, and changes in the capacity due to the acoustic vibrations are translated into capacity changes which lead to the electrical signals at the output of the microphone 23.

The capacitive change is caused by the acoustic waves of the sound passing through the holes 33a to 33e. The movable plate 25 flexes in response to the change in air pressure caused by the acoustic waves as indicated by the double arrow 35. The movable plate 25 thus acts like a membrane. The movement will modulate the gap 37 between the movable plate 25 and the stiff plate 31 which in turn also modulates the capacity between the two plates. The air in the chamber 39 formed between the substrate 29, the pillar structure 27a, 27b and the movable plate 25 flows out and back in via a ventilation path 41. The chamber 39 thus forms a kind of acoustic resonator which is linked to the outside of the sensing device 21 via the ventilation path 41.

The sensing device 21 furthermore comprises a gas sensing means 43 arranged over, in particular, on the microphone 23.

It comprises a gas sensitive layer 45 with a plurality of perforations 47a to 47e. In this embodiment, the perforations 47a to 47e are aligned with the perforations 33a to 33e of the microphone 23 along the thickness direction X of the sensing device 21. By doing so, the air or gas entering the sensing device 21, e.g. the breath of a user when the user talks or breaths into the electronic device, can reach the microphone 23. At the same time, the air or gas can be analysed using the same flow.

In this embodiment, the gas sensitive layer 45 is a metal oxide based sensing device. The detection principle is based on a change of the resistance of a thin film upon adsorption of the gas molecules on the surface of a semiconductor. One example of a metal oxide is tin oxide. According to variants of the invention, the gas sensing means 43 can comprise carbon nanotubes (CNTs), gold nanoparticles, a silicon nanowire, a quartz crystal microbalance (QCM), a colorimetric sensor, and a conductive polymer. Theses technologies have the advantage of low energy consumption. Selective and non selective technologies can be chosen and/or combined.

According to a variant of this embodiment, a common housing 51, illustrated in dashed lines in FIG. 2, can be used to package the microphone 23 and the gas sensing means 43 together into one device. The housing 51, preferably, has perforations 53a to 53 aligned with the perforations of the microphone 23 and the gas sensing means 43.

The sensing device 21 can be part of an array of devices or a stack.

FIG. 3 illustrates schematically a metal oxide gas sensing means 61 according to the invention. This metal oxide gas sensing means 61 could be used as gas sensing means 11 or 43. The metal oxide gas sensing means comprises a gas sensor hot plate 63 with perforations 65 and a gas sensing layer 67 with perforations 69. With the perforations 65 and 69 being aligned with each other, both sensing means, the microphone 23 and the gas sensing means 43 (see FIG. 2) face essentially the same environmental conditions concerning the entering gas flow, e.g. temperature, pressure, volume flow.

Like mentioned above gas molecules get adsorbed on the surface of the sensing layer 67 which changes the resistance of the layer. This signal can then be exploited for further gas analysis.

The sensing means 61 may comprise further layers or structures in particular electrical connections for outputting the signals as well as for power supply.

According to a variant, the hot plate can be directly formed in or on the last layer of the microphone 9 or 23 as shown in FIGS. 1 and 2 to further integrate the device.

FIG. 4 illustrates a block diagram of a further embodiment of the sensing device according to the invention. The sensing device 71 which can be the sensing device 7 or 21 of the above described embodiments comprises a common housing 73, an acoustic wave sensing means 75, e.g. the microphone 9 or 11, and a gas sensing means 77, e.g. the gas sensing means 11, 43 or 61. The perforations in the housing 73, the acoustic wave sensing means 75 and the gas sensing means 77 are not illustrated in the figure.

The sensing device 71 furthermore comprises an analog to digital converter (ADC) 79 and a processing unit 81 for signal treatment and analysis. The acoustic wave sensing means 73 outputs its signals to the ADC 79 which are then processed in the processing unit 81. The signal can then be output via the interface 83. The gas sensing means 75 also outputs its signals to the ADC 79 which are then processed in the processing unit 81. The signal can then be output via a second interface 85 or the same output interface 83 towards the processing unit of the portable device.

According to a variant, the acoustic wave sensing means 75 and the gas sensing means 77 can each have a dedicated ADC and/or a dedicated processing unit. According to yet another variant, the ADC and/or at least a part of the processing of the signals can be carried out in the portable device outside the sensing device.

FIG. 5 illustrates a further embodiment of the sensing device according to the invention. In this embodiment the sensing device 91 has an acoustic wave sensing means 93 and a gas sensing means 95 that are arranged side by side on a common substrate 97. Both sensing means are incorporated into a common housing 99 with perforations 101.

FIG. 6 illustrates a block diagram of a method to estimate the volume of a gas according to the invention. To carry out the method one of the sensing devices 7, 21, 71, 91 as described above could be used.

To determine the concentration of a certain molecule or a combination of molecules in a gas flow, the gas sensing means, e.g. 11, 43, 77 or 95 are configured to detect the presence of predetermined molecules in the flow, e.g. the breath of a user who breathes into the hole 15 of a personal electronic device like the one illustrated in FIG. 1. The acoustic wave sensing means, here in the form of a microphone 9, 23, 75 and 93, is then used to determine the volume so that the concentration of the molecules can be established. For instance, the sensing device can be configured such that the gas sensing means collects data up until a predetermined calibration volume has been entered the sensing device. As the gas sensing means and the acoustic wave sensing means are stacked onto each other, in particular aligned in the thickness direction X of the device, or positioned next to each other, they sense under essentially the same environmental conditions and "see" essentially the same gas volume.

FIG. 6 illustrates one embodiment of the method according to the invention. In the embodiment a sensing device 21 like illustrated in FIG. 2 and incorporated into the hole 15 of the personal electronic device 1 as illustrated in FIG. 1 will be used. Other sensing devices and other electronic devices could of course also be used.

When a user breaths into the hole 15 of the personal electronic device 1, the gas sensing means 43 will sense the presence of the gas and output corresponding signals towards the processing means 81 (step 113).

In parallel (step 115), the pressure exerted by the gas flow 49 onto the movable plate 25 of the acoustic wave sensing means 23 will move or deform the movable plate 25. This movement/deformation will be sensed based on a change of capacity.

The change in capacity can be used to determine the pressure and duration of the gas flow entering the sensing device 21 and from those parameters the volume of gas that entered the device can be estimated and/or calculated (step 117) and output to the processing means 81.

In the data processing step 119, the data obtained from the volume estimation and the gas sensing are then combined and processed such that the processing means can output the result of the measurement. As an example, the sensing device can output the concentration of alcohol in the breath of the user or the concentration of a certain molecule or a plurality of molecules indicative of a certain disease. Furthermore, the quality of ambient air surrounding the user could be analysed this way.

With the above described inventive devices and methods, it becomes possible to integrate gas sensing functionality into personal electronic devices without having to add an additional hole in the housing of the device. The user will blow into the same hole of his device in which he is used to talk into. Thus, the gas sensing can be carried out without that the user has to adapt to a new way of using his device. By using the acoustic wave sensing means, in particular the microphone, to calibrate the gas volume entering the personal electronic device, the use of a complicated mechanical gas volume calibration or a non reliably software based volume calibration can be prevented.

LIST OF REFERENCE NUMERALS 1 electronic device
3 housing
5 display device
7 sensing device
9 acoustic wave sensing means, microphone
11 gas sensing means
13 mother board
15 opening/hole
17 grid
21 sensing device
23 microphone
25 movable plate
27a,b pillar structure
29 substrate
31 fixed plate, stiff plate, back plate
33a-e perforations in the fixed plate
35 movement of the movable plate
37 air gap
39 air chamber
41 ventilation path
43 gas sensing means
45 gas sensitive layer
47a-e perforations
49 air or gas flow
51 sensing device's common housing
61 metal oxide gas sensing means
63 hot plate
65 perforations
67 gas sensing layer
69 perforation
71 sensing device
73 common housing
75 acoustic wave sensing means
77 gas sensing means
79 ADC
81 processing unit
83 output interface
85 output interface
91 sensing device
93 acoustic wave sensing means
95 gas sensing means
97 substrate
99 common housing
101 perforations
111 gas sensing method
113 step of receiving signals from gas sensing means
115 step of receiving signals from acoustic wave sensing means
117 step of estimating gas volume
119 step of data processing
X thickness direction of the sensing device

The invention claimed is:

1. Sensing device for a portable electronic device, the sensing device comprising:
an acoustic wave sensing mechanism comprising a microphone; and
a gas sensing mechanism,
wherein the acoustic wave sensing mechanism and the gas sensing mechanism are integrally formed in one device, and
wherein the acoustic wave sensing mechanism is provided over a substrate and the gas sensing mechanism is stacked over the acoustic wave sensing mechanism.

2. The sensing device according to claim 1, wherein the acoustic wave sensing mechanism and the gas sensing mechanism are incorporated into a common housing.

3. The sensing device according to claim 1, wherein the microphone is a microelectromechanical system (MEMS) microphone.

4. The sensing device according to claim 1, wherein the gas sensing mechanism comprises a plurality of perforations that are aligned with perforations of a fixed plate of the microphone in the thickness direction (X) of the acoustic wave sensing mechanism.

5. The sensing device according to claim 1, wherein the microphone comprises a membrane and wherein the sensing device is configured such that a reference volume of a gas sensed by the gas sensing mechanism is determined based on an electrical signal representative of a movement and/or deformation of the membrane.

6. The sensing device according to claim 5, wherein the membrane is a movable plate of the microphone.

7. The sensing device according to claim 1, further comprising an analog-to-digital converter and/or processing mechanism provided on said substrate, wherein the integrated microphone and gas sensing mechanism share at least partially said analog-to-digital converter and/or processing mechanism.

8. Sensing device for a portable electronic device, the sensing device comprising:
an acoustic wave sensing mechanism comprising a microphone; and
a gas sensing mechanism,
wherein the microphone comprises a membrane,
wherein the acoustic wave sensing mechanism and the gas sensing mechanism are integrally formed in one device,
wherein the gas sensing mechanism is based on at least one of tin oxide, carbon nanotubes (CNTs), a gold nanoparticle, a silicon nanowire, a quartz crystal microbalance (QCM), a colorimetric sensor, and a conductive polymer, and wherein the gas sensing mechanism is arranged in or on or over the membrane or in or on or over a fixed plate of the microphone; and wherein the sensing device is configured such that a reference volume of a gas sensed by the gas sensing mechanism is determined based on an electrical signal representative of a movement and/or deformation of the membrane.

9. A method for determining a volume of a gas in a gas flow using the sensing device of claim 8, comprising determining the volume of the gas in the gas flow based on an electrical signal representative of a movement and/or deformation of the membrane.

10. The method of claim 9, wherein the membrane comprises a movable plate of the microphone.

11. The method of claim 10, wherein the volume determination further comprises obtaining from the electrical signal pressure data relative to the pressure exerted by the gas flow on the membrane and/or timing data relative to a duration during which pressure is exerted on the membrane.

12. The method of claim 9, wherein the volume determination further comprises obtaining from the electrical signal pressure data relative to the pressure exerted by the gas flow on the membrane and/or timing data relative to a duration during which pressure is exerted on the membrane.

* * * * *